United States Patent [19]

Luczyk

[11] Patent Number: 5,456,261
[45] Date of Patent: Oct. 10, 1995

[54] CARDIAC MONITORING AND DIAGNOSTIC SYSTEM

[75] Inventor: William J. Luczyk, Waukesha, Wis.

[73] Assignee: Marquette Electronics, Inc., Milwaukee, Wis.

[21] Appl. No.: 168,538

[22] Filed: Dec. 16, 1993

[51] Int. Cl.$^6$ ................................................. A61B 5/0402
[52] U.S. Cl. ........................... 128/702; 128/696; 128/705
[58] Field of Search ....................................... 128/696, 702, 128/703, 704, 705; 364/413.06

[56] References Cited

U.S. PATENT DOCUMENTS

| | | | |
|---|---|---|---|
| 3,830,228 | 8/1974 | Foner | 128/696 |
| 4,531,527 | 7/1985 | Reinhold, Jr. et al. | 128/696 |
| 5,046,504 | 9/1991 | Albert et al. | 128/702 |
| 5,299,119 | 3/1994 | Kraf et al. | 128/696 |
| 5,313,953 | 5/1994 | Yomtov et al. | 364/413.06 |
| 5,318,037 | 6/1994 | Evans et al. | 128/696 |
| 5,339,823 | 8/1994 | Reinhold, Jr. et al. | 128/696 |

*Primary Examiner*—William E. Kamm
*Assistant Examiner*—Kennedy J. Schaetzle
*Attorney, Agent, or Firm*—Michael, Best & Friedrich

[57] ABSTRACT

A cardiac monitoring system includes an acquisition module for acquiring a plurality of analog cardiac signals through leads connected to predetermined locations on the body of a patient and for converting the cardiac signals to twelve standardized ECG lead signals. An arrhythmia monitor analyzes a plurality of the ECG signals for determining the existence of rhythm abnormalities and a twelve lead analyzer analyzes both the rhythm and the contours of all of the ECG lead signals for rhythming conduction, infarction, hypertrophy and repolarization abnormalities. The arrhythmia monitor and the twelve lead analyzers are operated concurrently for the simultaneous analysis of the ECG signals so that the occurrence of a rhythm abnormality and its cause can be determined on a real time basis.

9 Claims, 3 Drawing Sheets

CARDIAC MONITORING AND DIAGNOSTIC SYSTEM

BACKGROUND OF THE INVENTION

This invention relates to cardiac monitors, and more particularly to a system for simultaneous arrhythmia monitoring and ECG analysis on a real time basis.

Electrocardiographs for acquiring and analyzing multiple leads of conventional ECG are known. For example, electrocardiographs manufactured by Marquette Electronics, Inc. of Milwaukee, Wis., include a twelve lead software program called the 12SL ECG Analysis Program. Eight of the leads (I, II, V1–V6) are acquired directly and the remaining four (III, aVR, aVL and aVF) are derived using Einthoven's Law. Each lead of ECG can be considered a view of the heart from a different angle. The program also determines the origin of the predominate rhythm from major categories such as electronic artificial pacing, atrial flutter, ectopic atrial rhythm, sinus rhythm, junction rhythm and atrial fibrillation. In addition, the program analyzes the contour of the QRS waveform using conventional criteria for Wolff-Parkinson-White atrial hypertrophy, QRS abnormalities, ST abnormalities-QRS related, ST elevation abnormalities, ST depression abnormalities and T wave abnormalities. These allow the physician to determine the existence of rhythm abnormalities, conduction abnormalities, hypertrophy, infarction and repolarization. This prior art program acquires ECG data for non real time or delayed analysis.

Cardiac monitors are also well-known for analyzing cardiac arrhythmia or beat irregularities. One such system is the EK-Pro arrhythmia analysis algorithm sold by Marquette Electronics, Inc. of Milwaukee, Wis. This system analyzes four ECG leads (I, II, III and V1) to determine the occurrence of such conditions as ventricular asystole, ventricular fibrillation, ventricular tachycardia, VT3-5, R-on-T, ventricular bradycardia, couplet, bigeminy, accelerated ventricular rhythm, pause, trigeminy, premature ventricular complexes, ST deviation, tachycardia, bradycardia, and irregular beats.

Arrhythmia monitors are generally rhythm sensing systems which can indicate the occurrence of and classify arrhythmias on a real time basis, but do not indicate their cause. ECG lead analyzers, on the other hand, can determine the condition of the entire myocardium. Present practice is to employ an arrhythmia monitor for triggering an alarm upon the occurrence of an arrhythmia. The patient will then be connected to an electrocardiograph in an attempt to determine its cause. However, in certain situations, such as upon the occurrence of an acute infarction, the patient is at highest risk during the initial stages of the infarct when an area of the myocardium is jeopardized due to ischemia but before the myocardium is damaged. This condition directly leads to a high probability of ventricular arrhythmia during the time when the patient's heart is already suffering from a lack of oxygenated blood. However, such an ischemic episode will not be detected by an arrhythmia monitor prior to the occurrence of ventricular arrhythmia.

SUMMARY OF THE INVENTION

It is an object of the invention to provide a new and improved system for heart monitoring and ECG analysis.

Another object of the invention is to provide a system for simultaneously detecting the occurrence of arrhythmias and for indicating their cause.

A further object of the invention is to provide a system for ECG analysis and arrhythmia detection on a real time basis.

In general terms, the invention comprises a cardiac monitoring system including means for acquiring a plurality of analog cardiac signals through leads connected to predetermined locations on the body of a patient and for converting said cardiac signals to a plurality of standardized ECG lead signals, first analyzing means for analyzing a first group of the ECG signals for determining the existence of rhythm abnormalities, second analyzing means for analyzing the contours of all of the ECG lead signals for conduction, infarction, hypertrophy and depolarization abnormalities, and means for simultaneously actuating the first and second analyzing means for the simultaneous analysis of the first group of ECG signals and the plurality of ECG signals whereby the occurrence of a rhythm abnormality and possible causes can be determined concurrently on a real time basis.

DETAILED DESCRIPTION OF THE PREFERRED EMBODIMENT

Figure 1:
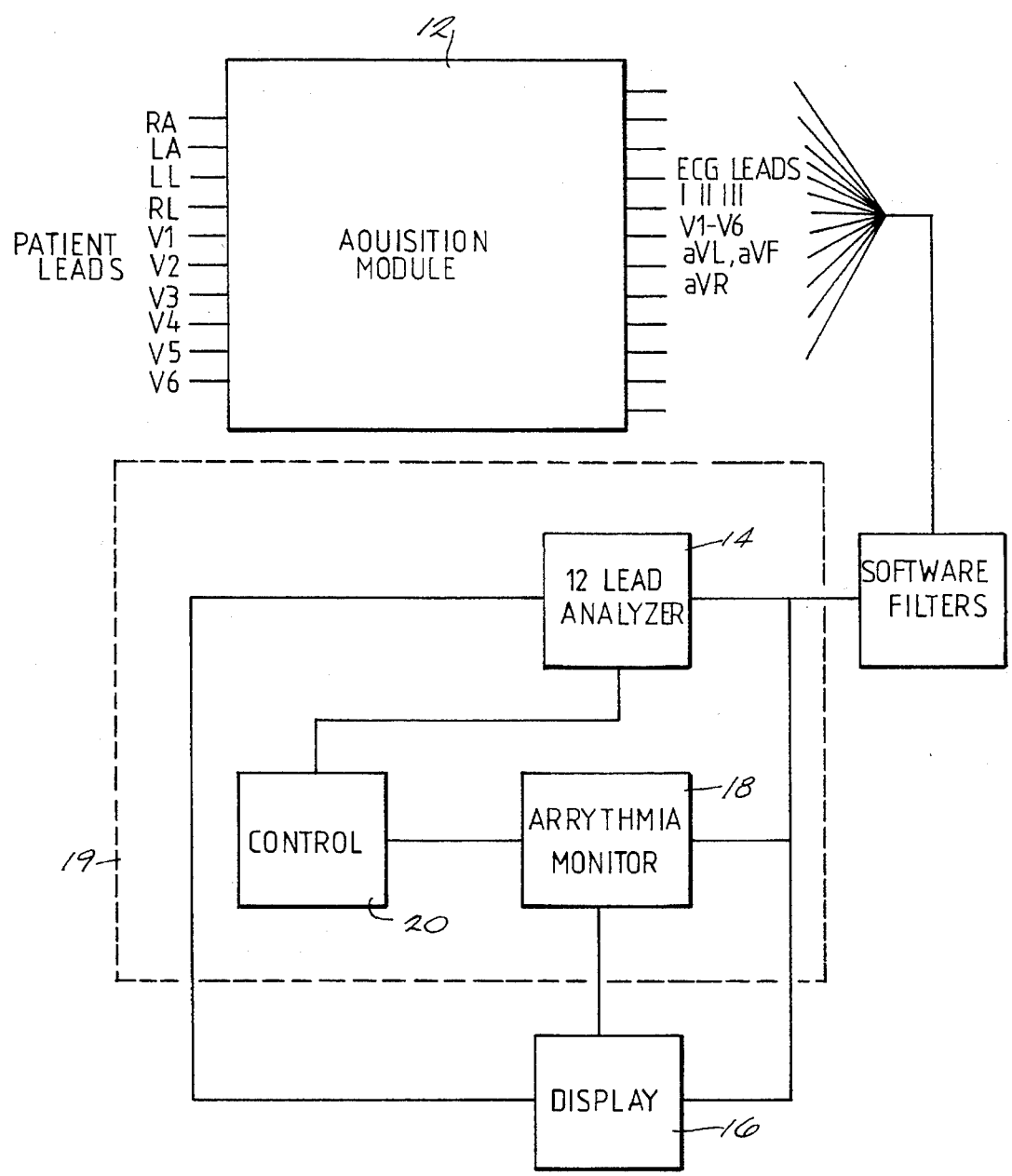
FIG. 1 schematically illustrates the cardiac monitoring and diagnostic system according to the preferred embodiment of the invention.

FIG. 1 schematically illustrates the cardiac monitor and twelve lead analyzing system according to the present invention. The system includes a conventional data acquisition module 12 which is connected to the patient by ten lead wires RA, LA, LL, RL, V1, V2, V3, V4, V5 and V6. The acquisition module 12 includes conventional common mode rejection and filters for removing patient breathing and muscle artifacts. The acquisition module also converts the analog lead signals to digital signals and generates the ECG leads I, II, V1, V2, V3, V4, V5 and V6 which are acquired directly from the patient leads and leads III, aVR, aVF, and aVL which are derived. The twelve digitized ECG signals are provided to a twelve lead analyzer 14 and a display 16 and the leads I, II, III and V1 are provided to an arrhythmia analyzer 18. The outputs from the twelve lead analyzer 14 and the arrhythmia analyzer 18 are provided to the display 16 which may also provide printed reports and may include alarms for the arrhythmia analyzer 18. While a twelve lead analyzer is employed in the preferred embodiment, those skilled in the art will appreciate that analysis programs for greater or lesser numbers of leads may also be employed without deviating from the invention.

The data acquisition module 14 and the arrhythmia monitor exist as software in the RAM/ROM of a central processing unit 19. The arrhythmia software may, for example, comprise the EK-PRO arrhythmia analysis algorithm and the twelve lead software may comprise the 12SL ECG Analysis Program, both of which are products of Marquette Electronics, Inc., of Milwaukee, Wis. The central processing unit also includes a control module 20 which permits the operator to operate the arrhythmia monitor 18 and the twelve lead analyzer selectively or concurrently. The control 20 may also be programmed to actuate the twelve lead analyzer 18 upon the receipt of an arrhythmia call or alarm signal from the arrhythmia monitor.

Figure 2:
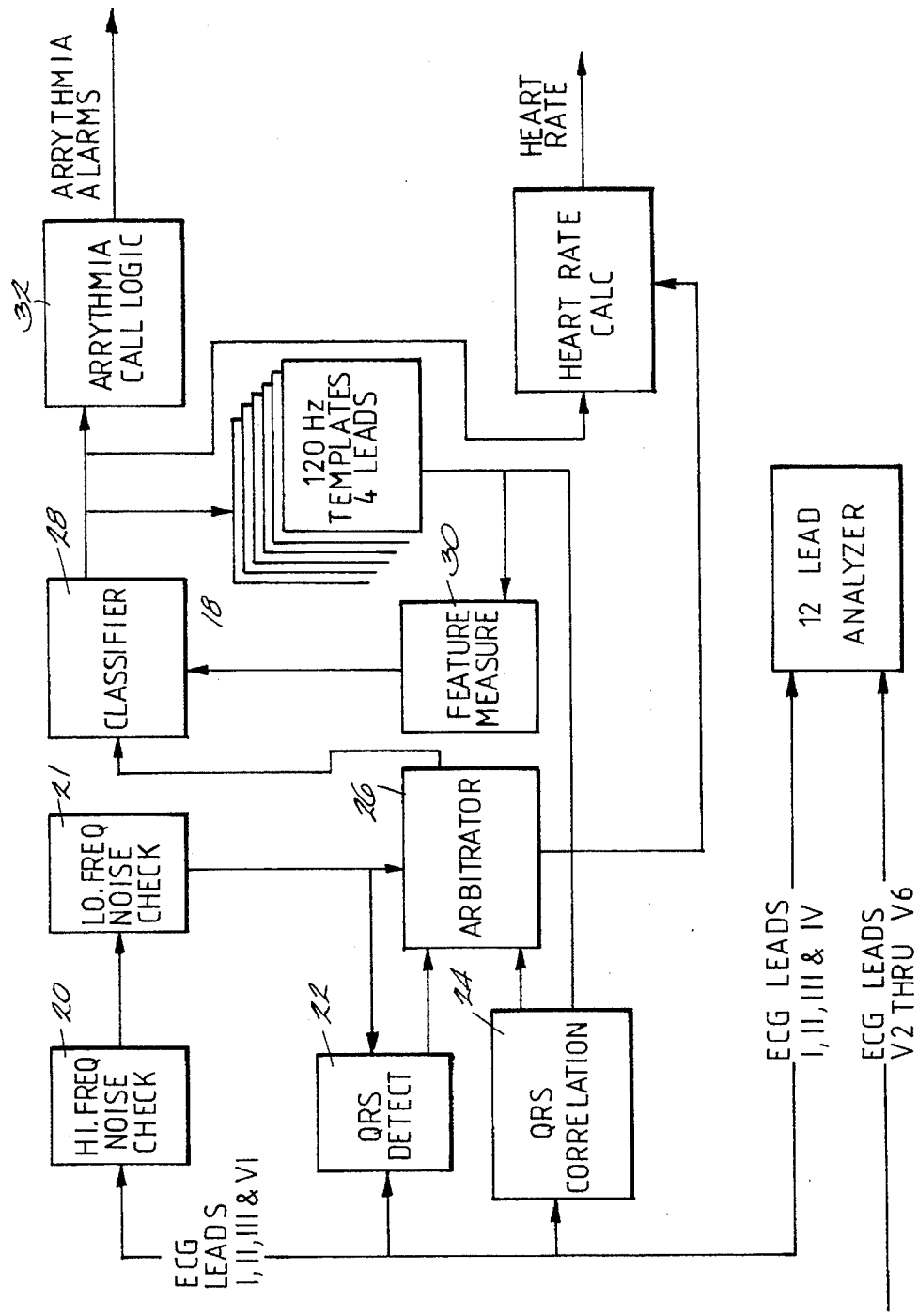
FIG. 2 schematically illustrates the arrhythmia analyzer of the system illustrated in FIG. 1.
Figure 3:
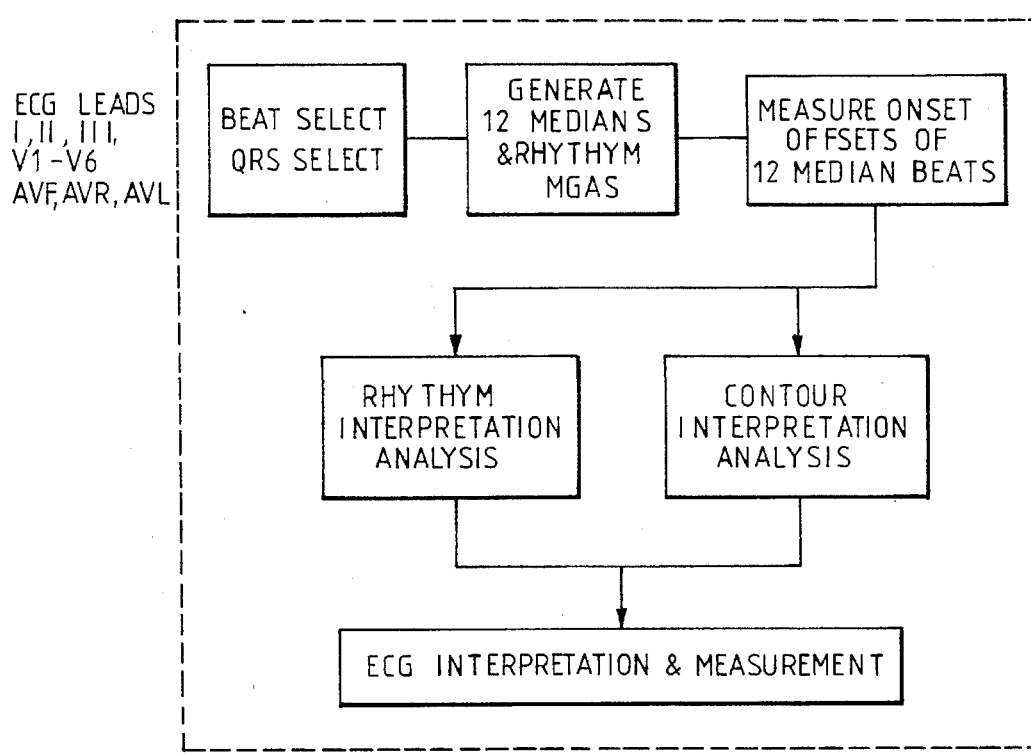
FIG. 3 schematically illustrates the ECG wave contour analyzer of the system illustrated in FIG. 1.

The arrhythmia analyzer 18 is shown in FIG. 2 to include a high frequency noise check module 20, a low frequency noise check 21, a QRS detect module 22, a QRS correlation module 24 and an arbitrator or module 26. The high frequency noise check module 20 and the low frequency noise check module 21 respectively evaluate each of the leads for high frequency and low frequency noise, which if present, deactivates the lead so that it is not further processed. The QRS detection module 22 detects signals falling within the physiologic band and which it recognizes as valid ECG signals. The QRS correlation 24 passes the ECG data stream through a list of active templates, which are incrementally updated so that they are progressively changed along with the beat shape.

The arbitrator module 26 processes beats recognized by the QRS correlator 24 and beats which do not match any of the existing templates, as determined by the detection module 22, and a determination is made whether to create a new template and replace the least useful of the active templates. These would be templates which are matched with the least frequency or have not been recently matched or classified as likely to be artifacts.

A classifier module 28 receives the template information associated with the beats and takes all the feature and temporal measurements and arrives at a determination as to what is represented by that particular beat, that is a normal QRS, an atrial artificially paced normal QRS, a premature supraventricular QRS, ventricular artificially paced QRS, a ventricular premature QRS, a T wave, a P wave, a ventricular artificial pacing spike, an atrial artificial pacing spike or an artifact. The measurements made to determine individual beat characteristics are R amplitude, S amplitude, QRS polarity, T wave polarity, ST segment, noise level, PR interval, P wave presence, QT interval, QRS duration, RR interval, RR interval variance, pacemaker signals and rotation of cardiac vector.

An arrhythmia call logic module 32 employs well-known criteria to make an arrhythmia call. These include the duration of usable ECG data, heart rate, the time between QRS complexes, the occurrence of a ventricular complex within a repolarization period, the occurrence of one or more ventricular beats preceded or followed by nonventricular beats, ST deviations of a predetermined magnitude, R-to-R intervals and the intervals between the QRS complex and a pacemaker spike. With this information, the arrhythmia call logic 32 can determine if one of the following has occurred: an artifact, ventricular asystole, ventricular fibrillation, ventricular tachycardia, VT3-5, R-on-T, ventricular bradycardia, couplet, bigeminy, accelerated ventricular rhythm, pause, trigeminy, isolated premature ventricular complexes, ST deviation, tachycardia, bradycardia, irregular heartbeat or electronic pacemaker nonsensing. If an arrhythmia call is indicated, an appropriate alarm signal is provided to the display 16 and the control 20.

The twelve lead analyzing section 40 receives the ECG leads I, II, III, V1–V6, aVF, aVR, and aVL. Initially, the beat select section makes a template for each lead. From this point on, the QRS selector looks for the same shape. If it finds a match, the program classifies it as another QRS detection. In addition, the program slides the wave forms past one another looking for the optimal match. If the output of the filters in the acquisition modules exceed a preselected value, but there is no match, it is assumed that a different beat type has been detected and an additional set of templates are made for further matching tests. Thus, the beat selector 42 uses a filter and template matching techniques to both detect and group by shape the QRS complexes which occur in the ECG record. The QRS detector also defines the points on the ECG record that can be used to align and time with maximum correlation, the respective beats of a beat type.

The program then determines which beat type will be used for the morphology measurements. The program uses the RR intervals and the location of any pacer spikes in order to decide which beat has the highest level of origin in the conduction system. Identical QRS shapes can even be subdivided as in the case of a sinus rhythm with premature beats. The selection is not dependent upon the number of beats per beat type but rather the beat type which is the most informative for analysis is the one sought after and any beat type with three or more complexes can qualify. The beat type that the computer considers to be most informative of normal conduction is often referred to as the primary beat.

After a primary beat has been chosen, each of its associated beats is used in generating a representative complex for each lead. This is done using the sample times generated by the QRS detector. These times not only indicate the occurrence of a QRS but also indicate when the QRS for a specific beat type are optimally matched. The representative complex is then generated with the median voltages from the aligned group of beats, that is, it is formed by taking, at each sample time, the middle voltage of the superimposed beats.

After the median for the primary cycle has been established for each of the twelve leads, the waves of each complex are identified. This is done separately for each lead. The program finds the points at which the signal crosses the baseline within each complex. If the crossing points define a wave that has an area greater than a predetermined value, the wave is considered to be significant. If the area is less than this value, the program considers the wave to be insignificant and it will not label it as a separate wave. The measurement matrix contains the amplitudes, with respect to QRS onset, and durations of all of the individuals waves, including the amplitude and duration of the P, P', Q, R and S waves, the amplitude of the T wave, the PR and QT intervals, the QRS duration and the STJ, STM and STE amplitudes.

The program then utilizes these measurements in making an interpretation. This includes a rhythm analysis and a morphology interpretation. The rhythm analysis first determines the origins of the predominant rhythm in the sample and chooses from the major categories consisting of electronic atrial pacing, atrial flutter, ectopic atrial rhythm, sinus rhythm, junction rhythm and atrial fibrillation.

The morphology interpretation will determine the existence of Wolff-Parkinson-White, atrial hypertrophy, QRS abnormalities such as low voltage QRS, pulmonary disease pattern, QRS axis, conduction abnormalities, ventricular hypertrophy, infarction, ST+ T abnormality with ventricular hypertrophy, dating infarcts, epicardial injury, pericarditis, early repolarization, nonspecific ST elevation, subendocardial injury, nonspecific ST depression, digitalis effect, junctional ST depression, ischemia, QRS-T angle and QT interval.

The twelve lead system 40 can be operated independently of the arrhythmia analyzer 18 or it can be operated on a real time basis along with the arrhythmia analyzer for analyzing the same ECG signals or its operation can be triggered automatically by an arrhythmia alarm signal from the arrhythmia call logic module 32.

The arrhythmia analyzer 18 indicates the occurrence of and classifies arrhythmias, but does not indicate their cause. The twelve lead analyzer 40, on the other hand, can determine the condition of the entire myocardium. If the two are operated concurrently on a real time basis, for simultaneously analyzing the same ECG signals, it may be possible to determine the cause of any arrhythmia detected by the arrhythmia monitor 18. For example, episodes such as ischemia may be detected at an early stage before the myocardium is damaged.

Also, because each of the twelve ECG leads is a view of the cardium along a different axis, the location of an infarct is indicated by wave abnormalities in specific leads. For example, septal myocardial infarction is indicated in leads V1 and V2; anterior myocardial infarction in leads V2, V3 and V4, lateral myocardial infarction in leads I, V5, V6 and aVL, inferior myocardial infarction produces an ST elevation in leads II, III and aVP. With the twelve lead analysis and the simultaneous detection and classification of arrhythmias, the cardiologist is able not only to detect the occurrence of an arrhythmia but to simultaneously determine its cause because both systems are running simultaneously and are analyzing the same ECG lead data on a real time basis.

While only a single embodiment of the invention as been illustrated and described, it is not intended to be limited thereby but only by the scope of the appended claims.

I claim:

1. A method of cardiac monitoring including the steps of acquiring a plurality of analog cardiac signals through leads connected to predetermined locations on the body of a patient, converting said cardiac signals to a plurality of standard digitized ECG lead signals, analyzing a first group of said ECG signals for determining on a real time basis the existence of rhythm abnormalities in the patient's heartbeats, and simultaneously with the analysis of said first group of ECG signals for rhythm abnormalities also analyzing the contours of all of said ECG lead signals, including the signals of said first group of ECG signals, for contour abnormalities including, conduction, infarction, hypertrophy and repolarization abnormalities whereby the occurrence of a rhythm abnormality and its cause can be determined concurrently.

2. The method set forth in claim 1 wherein twelve ECG lead signals are analyzed for contour abnormalities.

3. The method set forth in claim 2 wherein said first group of ECG lead signals comprise leads I, II, III and V-1 and all of said ECG lead signals comprise said first group of ECG signals plus V2–V6, aVR, aVL, and aVF.

4. A cardiac monitoring system including means for acquiring a plurality of analog cardiac signals through leads connected to predetermined locations on the body of a patient, means for converting said cardiac signals to a plurality of standardized ECG lead signals, first analyzing means for analyzing a group of said ECG signals for determining the existence of rhythm abnormalities, second analyzing means operable simultaneously with said first analyzing means for analyzing the contours of all of said ECG lead signals, including said first group of signals for contour abnormalities, conduction, infarction, hypertrophy and repolarization abnormalities, and a means for simultaneously actuating said first and second analyzing means for the simultaneous analysis of said group of ECG signals and all of said ECG signals whereby the occurrence of a rhythm abnormality and its cause can be determined concurrently.

5. The cardiac monitoring system set forth in claim 4 wherein said first and second analyzing means are operative to analyze simultaneously said ECG signals on a real time basis.

6. The cardiac monitoring system set forth in claim 5 wherein said ECG lead signals comprise twelve standardized signals.

7. The cardiac monitoring system set forth in claim 6 wherein said first analyzing means is operative to analyze twelve ECG lead signals.

8. A method of cardiac monitoring including the steps of acquiring a plurality of analog cardiac signals through leads connected to predetermined locations on the body of a patient, converting said cardiac signals to a plurality of standard digitized ECG lead signals, analyzing a first group of said ECG signals for determining on a real time basis the existence of rhythm abnormalities in the patients heartbeats, and simultaneously with the analysis of said first group of ECG signals analyzing the contours of all of said ECG lead signals, including the first group of ECG signals, for contour abnormalities in the same heartbeats, whereby the occurrence of a rhythm abnormality can be determined from the rhythm analysis and its cause can be determined concurrently from the contour analysis.

9. The method set forth in claim 8 wherein twelve ECG lead signals are analyzed for contour abnormalities.

* * * * *